United States Patent [19]

McRae

[11] Patent Number: Plant 5,981

[45] Date of Patent: May 12, 1987

[54] ASIATIC LILY PLANT NAMED 'FORERUNNER'

[75] Inventor: Edward A. McRae, Boring, Oreg.

[73] Assignee: Melridge Inc., Gresham, Oreg.

[21] Appl. No.: 771,579

[22] Filed: Aug. 30, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new variety of hybrid lily plant particularly characterized by the rich orange color tone of its flowers and lack of spotting, as well as their unusually large size borne in large clusters of flowers having excellent form, strong color and long persistence, both on the plant and as cut flowers, these being features which are completely new in the upright Asiatic division of lilies suited to forcing and mass commercial cultivation. The new plant is highly resistant to disease and shows high tolerance of virus and is an excellent garden plant. Also, its bulbs may be precooled and forced for cut flower production, the clone being extremely vigorous and a good grower and propagator.

1 Drawing Figure

BACKGROUND OF THE NEW PLANT

My new variety of lily plant originated as a seedling selected from a group of seedlings resulting from my crossing of the clonal cultivar "Sunstar" with the clonal cultivar "Connecticut King" (unpatented) at Sandy, Ore., in the course of breeding efforts carried on by me since 1975. The breeding efforts in this case had the objective of producing spotless upright Asiatic lilies in shades of gold and orange well suited for forcing for cut flower production out of season.

This new variety of lily plant has been asexually reproduced by me and under my direction at Sandy, Ore., and successive generations of this plant, produced by bulb scale propagation and natural propagation from bulblets, have demonstrated that the new variety possesses all of the desired characteristics of excellence of form, color, and habit, the flowers being of large size produced on a single stalk. The clone of this plant is a vigorous and good grower and propagator as observed at Sandy, Ore., the successive generations demonstrating that the novel and distinctive characteristics of the new variety are fixed and hold true, under asexual propagation, from generation to generation.

DESCRIPTION OF THE DRAWING

My new variety of lily plant is illustrated by the accompanying photographic drawing which shows an open bloom with buds and foliage and illustrates the flower form and tepal arrangement and, in particular, the novel and distinctive orange color tone which has been hand painted on the drawing to truly show the specified colors.

DESCRIPTION OF THE NEW VARIETY

The foregoing is a detailed description of my new variety of Asiatic hybrid lily with nomenclature according to The International Lily Register, Second Edition, of The Royal Horticultural Society of London, England, the color designations being according to The R.H.S. Colour Chart of The Royal Horticultural Society of London, England, published in 1966.

THE PLANT

Origin: Seedling.

Parentage:

*Seed parent.*—Lilium "Sunstar".

*Pollen parent.*—Lilium "Connecticut King" (unpatented).

Classification:

*Horticultural.*—Division I-A, Upright Asiatic Hybrid Lily, according to the Horticultural Classification of Lilies by The Royal Horticultural Society.

*Commercial.*—Asiatic Hybrid Lily.

Form: Single stem, erect and stately.

Height: About 80 to 90 cm. from bulbs about 15 to 18 cm. in circumference, when light levels are adequate. (Low light levels cause "stretching".).

Growth: Vigorous and upright.

Foliage:

*Quantity.*—Abundant.

*Leaf size.*—About 8 to 12 cm. long and about 1 to 2 cm. wide.

*Leaf shape.*—Lanceolate with acuminate tip and entire margins.

*Texture.*—Leathery.

*Aspect.*—Glossy.

*Color.*—Upper surface, medium green. Lower surface, light green.

Bulb size: Various, ranging up to 25 cm. in circumference in commercial use.

Color: White.

THE BUD

Form: Long and obtuse ovoid.

Size: About 8 to 9 cm. long and about 5 to 7 cm. in circumference just prior to opening.

Opening rate: The mature bud opens slowly in response to light; this takes about one hour.

Color: The outside or lower tepal surface color is soft green shading into orange, RHS 24-C, just prior to opening and as the tepals begin to unfurl.

Peduncle: Erect in character and about 6 to 8 cm. long.

*Color.*—Medium green with light plum overlay.

THE FLOWER

Blooming habit: Annually, once and profusely, in mid-season for Asiatic lilies.

Size: Usually large, about 16 to 19 cm. in diameter, the outer tepals being about 2.5 to 3 cm. wide and the inner tepals being about 3.5 to 4.5 cm. wide.

Borne: In clusters of 12 to 20 blooms as a raceme on a stocky stem from a bulb of about 18 to 21 cm. in circumference.

Shape: Somewhat flattened cup-shape with slightly recurved tepal tips and slightly ruffled tepal margins.

Tepalage:

Number.—Six.

*Arrangement.*—Imbricated.

*Appearance.*—Shiny.

*Color.*—The basic color is RHS 24-A/B with tepal tips shading into yellow-orange, 23-B, the area above the nectary furrows being about 2 cm. long and 2 cm. wide and showing a deeper tone of orange, 25-A/B. The nectaries are covered with very short white pubescence.

Spotting: None.

Color changes: The flower becomes slightly less yellow-orange and more orange as the flowers age.

Tepal Longevity: Tepals stay on the stem for about three weeks.

Pedicels: Average length about 4 to 8 cm. with the secondary pedicels being the shortest.

*Color.*—Medium green with light plum overlay.

*Character.*—Sturdy and ascending at 45° angle from the stem axis. Secondary buds are present.

Fragrance: None.

Disease resistance: The flower and plant are resistant to disease and in particular, they are resistant to Fusarium bulb rot and to Botrytis blight, as observed in western Oregon.

Lasting quality: The flower is long lasting, both on the plant and as a cut flower.

THE REPRODUCTIVE ORGANS

Stamens:

*Number.*—Six.

*Arrangement.*—Typical of genus Lilium.

Anthers (dehisced) and pollen:

*Color.*—Grayed orange, RHS 170-A.

Filaments:

*Length.*—About 5 cm.

*Color.*—Soft orange, RHS 25-C/D.

Pistils: One in number.

*Length.*—About 5 cm.

Stigma:

Size.—Large.

Color.—Soft orange, RHS 25-C/D.

THE FRUIT

Fertility: The fruit is fertile.

Shape: Ovoid.

Color at maturity: Soft brown, sometimes overlaid with soft plum.

This new lily plant is characterized by the upright orientation of its flowers which are of an unusually large size and tepal thickness, with an absence of spotting, and a rich, mellow orange color tone. In addition, the clone possesses to a high degree the desirable characteristics of hybrid vigor, great hardiness, and disease resistance, as well as the characteristics of excellence of form, color and habit.

This new variety of Asiatic hybrid lily most nearly resembles "Croesus" (unpatented) but has much larger flowers with broader and thicker tepals and no spotting. The color of the new variety is more intense than that of "Croesus".

I claim:

1. A new and distinctive variety of Asiatic hybrid lily plant substantially as herein shown and described, characterized by its large sized flowers with rich orange color and unspotted tepals; the excellence of its flower form; its versatility both as a garden plant and as a cut-flower plant produced under glass and out of season from forced precooled bulbs; and by its vigorous growth and rapid natural propagation.

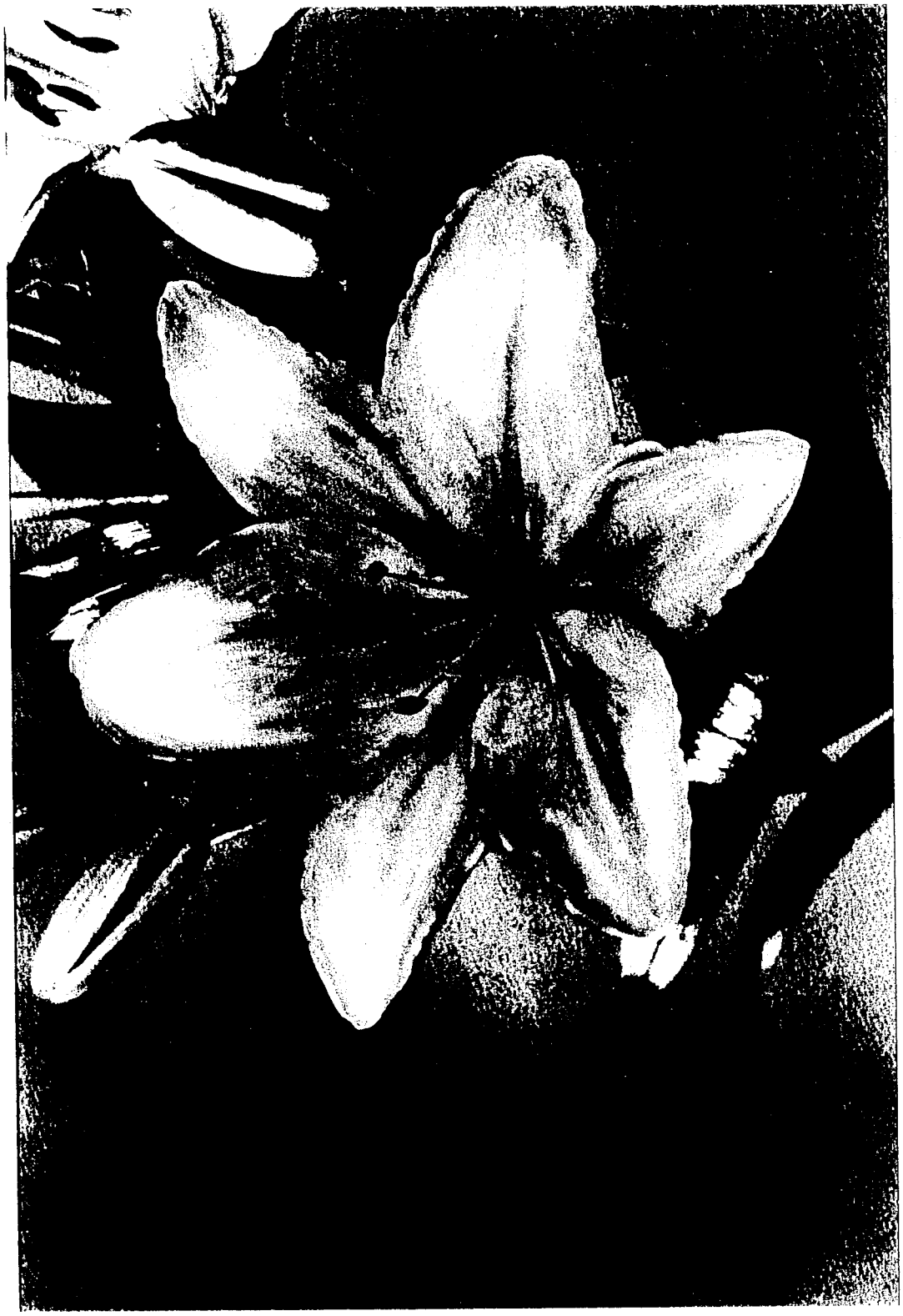

* * * * *